United States Patent [19]

Matsueda et al.

[11] Patent Number: 4,927,916

[45] Date of Patent: May 22, 1990

[54] METHOD OF PRODUCING FIBRIN-SPECIFIC MONOCLONAL ANTIBODIES LACKING FIBRINOGEN-CROSS-REACTIVITY USING FIBRIN-SPECIFIC PEPTIDES

[75] Inventors: Gary R. Matsueda, Winchester; Edgar Haber, Weston; Kwan Hui, Brighton, all of Mass.

[73] Assignee: The General Hospital Corporation, Boston, Mass.

[21] Appl. No.: 824,228

[22] Filed: Jan. 30, 1986

Related U.S. Application Data

[63] Continuation-in-part of Ser. No. 603,155, Apr. 23, 1984, abandoned.

[51] Int. Cl.$^5$ .................. C07K 15/14; A61K 39/395; I07K 15/04; C12N 35/00
[52] U.S. Cl. ........................... 530/387; 530/382; 530/380; 530/329; 530/806; 530/807; 530/808; 530/809; 530/812; 435/70.21; 435/172.2; 435/240.27; 935/93; 935/95; 935/104; 514/16; 424/85.8
[58] Field of Search ............... 530/387, 806, 382, 329; 435/240.26, 240.27, 172.2, 68; 935/93, 104, 95; 514/16

[56] References Cited

U.S. PATENT DOCUMENTS

| | | | |
|---|---|---|---|
| 4,147,765 | 4/1979 | Stephan et al. | 530/382 |
| 4,455,290 | 6/1984 | Olexa et al. | 530/382 |
| 4,722,903 | 2/1988 | Kudryk et al. | 530/387 |
| 4,758,524 | 7/1988 | Bundeson et al. | 435/7 |

FOREIGN PATENT DOCUMENTS 0063002 10/1982 European Pat. Off. ............ 530/382

OTHER PUBLICATIONS

Hui et al., Science, 222, 1129–1132, (12/9/83).
Pacella et al., Mol. Immunol., ZO(5), 521–7, (May 1983).
Matsueda et al., *Pept Struct Funct*, Proceeding 8th Am. Pept Symp, Hniby (ed), pp. 873–876, (1983).
Kudryk et al., 21(1), 89–94, (Jan. 1984).
Houranish et al., Fed. Proc., 44, p. 1846, AB8381, (1985).
Bode et al., Science, 229, 765–767, (Aug. 1985).
Scheefers–Borchel et al., PNAS, 82, 7091–7095, (1985).
Hessel et al., Eur J. Bioch, 98, 521–534, (1979).
Nossel, Nature, 291, 165–168, (1981).
Matsueda et al., Fed Proc, 42, p. 1992, A61375, (Jun. 1983).
Thorpe et al., Hybridoma, 3(4), pp 381–385, (Winter 1984).
Whitaker et al., Pathology, 16(3), p. 357, (Mar. 1984).
Sobel et al., Thromb Haemostasis, 46(1), 240, (1981).
Soria et al., Ann. N.Y. Acad. Sci., 408, 665–666, (1983).
Kudryk et al., 20(11), pp. 1191–1200, (Nov. 1983).
Rosebrough et al., Radiol., 156, pp. 515–517, (1985).
Matsueda et al., Haemostasis, 14(1), 44, (1984).

*Primary Examiner*—Margaret Moskowitz
*Assistant Examiner*—Jeff Kushan
*Attorney, Agent, or Firm*—Saidman, Sterne, Kessler & Goldstein

[57] ABSTRACT

Peptides comprising fibrin-specific epitopic sequences are used to prepare hybridoma cell lines producing antifibrin-specific monoclonal antibodies substantially devoid of fibrinogen-cross-reactivity obtained by somatic cell fusion. The antibodies are useful for the in vivo and in vitro detection of thrombi and fibrin deposits.

3 Claims, 2 Drawing Sheets

METHOD OF PRODUCING FIBRIN-SPECIFIC MONOCLONAL ANTIBODIES LACKING FIBRINOGEN-CROSS-REACTIVITY USING FIBRIN-SPECIFIC PEPTIDES

This work was supported by National Institutes of Health Grant Number HL-28015. The U.S. Government has certain rights in this invention.

CROSS REFERENCE TO RELATED APPLICATION

The present application is a continuation-in-part of application Ser. No. 603,155, filed in the United States Patent and Trademark Office on Apr. 23, 1984, abandoned.

BACKGROUND OF THE INVENTION

1. Field of the Invention

The present invention relates to synthetic peptides capable of eliciting fibrin-specific antibodies free of fibrinogen cross-reactivity. This invention also relates to hybridoma cell lines secreting antifibrin-specific monoclonal antibodies free of cross-reactivity with fibrinogen, the circulating fibrin precursor. These antibodies have been found to be useful as agents for the in vivo localization of fibrin deposits and the detection of thrombi in humans and other animals.

2. Description of the Background Art

In vivo immunodetection of thrombi and fibrin deposits remains an important clinical problem. In humans, the detection and localization of deep vein thrombi and coronary artery thrombi are two clinically important problems.

Blood clots when thrombin cleaves two pairs of small peptides from fibrinogen to yield fibrin monomers (Blomback, B. and Vestermark, A., *Ark. Kemi* 12: 173 (1958) and Doolittle, R. F., *Adv. Protein Chem.* 27: 1 (1973)). Fibrin monomers spontaneously aggregate to form an insoluble gel, which is then covalently stabilized by Factor XIIIa. Despite the dramatic differences between the two, fibrin retains 98% of the original covalent structure of fibrinogen. Thus, it is understandable that antifibrin serum cross-reacts strongly with fibrinogen, and that only one instance is known where a fibrin-specific serum was produced (Bosnjakovic, V. B. et al., *Lancet* 2: 452 (1977)).

Polyclonal antibodies raised against fibrin or fibrinogen have been utilized for localizing a variety of tumors, in particular the fast-growing kind (Day, E. D., et al., *J. Natl. Cancer Insti.* 22: 413 (1958), Bale, W. F., et al., *Cancer Res.* 20: 1488 (1960), Pressman, D., *Cancer Res.* 40: 2965 (1980)). However, these antibodies all showed to some extent cross-reactivity with fibrinogen.

Polyclonal antibodies to fibrin-fibrinogen, to fibrinogen alone or to degradation products of both polypeptides have been developed for use in the detection of venous thrombosis in humans (Reich, T., et al., *Surgery* 60(6): 1211, Spar, I. L., et al., *Circulation Research,* XVII: 322 (1965), and Stephan, W., et al., U.S. Pat. No. 4,147,765). In Reich, T., et al. and Spar, I. L., et al., supra, the radiolabelled antibodies had a substantial degree of fibrin-fibrinogen cross-reactivity. In the Stephan, W., et al. reference, the antiserum was elicited by immunological challenge with the early fibrin and fibrinogen degradation products formed by the action of plasmin on fibrin and fibrinogen, and referred to in the literature as fibrinogen S (fg-X), and fibrinogen Y (fg-Y).

A different approach for the detection of deep-vein thrombosis was undertaken by Knight, L. C., et al., *J. Nuclear Med.* 19(8): 891 (1978) by radio-iodinating fibrinogen. This method, however, was found to be inferior to the labelling of platelets with $^{111}$In, for the localization of thrombi in deep-vein thrombosis.

When plasminogen is converted by an activator to plasmin, the active fibrinolytic enzyme of plasma, it develops a marked affinity for its substrate, fibrin. Ouchi, H. and Warren, R., *Surgery* 51(1): 42 (1962), discovered that this affinity might be put to use by tagging plasminogen with a radioactive isotope and using it as a tracer to seek out intravascular clots. However, the $^{131}$I-labelled plasminogen showed a somewhat depressed fibrinolytic activity (28.6%).

Pilgeram, L., U.S. Pat. No. 4,245,040 improved on an earlier method for detecting circulating fibrin (Lorand, L., in *Fibrinogen and Fibrin Turnover of Clotting Factors,* Ed. Koller F., F. K. Schattauer Verlag-Stuttgart, 1963; and Kisker, C. D. and Rush, R., in "Detection of Intravascular Clotting," *J. Clin. Investig.* 50:2235 (1971)). Pilgeram's improvement consisted in attaching an isotopic label to the soluble circulating fibrin, by means of a Factor XIII-containing glycine-C$^{14}$ ethyl ester. However, it is recognized that the use of antifibrin antibodies which crossreact with fibrinogen is limited.

Although not previously done in the case of the fibrin molecule, synthetic peptides corresponding to portions characteristic of certain antigens have been prepared. For example peptides corresponding to carcinoembrionic antigen (CEA) are known in the prior art, and have been used for raising antibodies (Sela, M., et al., U.S. Pat. No. 4,075,194). The thus raised antibodies were intended for use in the detection of adenocarcinomas of the digestive tract, pancreas and breast.

A need continues to exist for highly specific antifibrin monoclonal antibodies and for synthetic epitopic peptides capable of raising such nonfibrinogen-cross-reacting antibodies. The antibodies would be useful for the in vivo detection of thrombi and fibrin deposits.

SUMMARY OF THE INVENTION

The present invention relates to synthetic epitopic peptides of variable length capable of eliciting fibrin-specific antibodies free of fibrinogen cross-reactivity. The invention also relates to hybridoma cell lines capable of secreting monoclonal antibodies against fibrin, which are free of fibrinogen-cross-reactivity. The fibrin-specific monoclonal antibodies are useful for the in vivo and in vitro detection of thrombi and fibrin deposits in humans, and other animals.

Also part of the invention is a method for the in vivo and in vitro detection of thrombi and fibrin deposits.

Various other objects, features and attendant advantages of the present invention will be more fully appreciated as the same becomes better understood from the following detailed description when considered in connection with the accompanying drawings.

Effect of fibrinogen on the direct binding of monoclonal antibodies secreted by hybridoma cell lines 59D8, 55D10 and 64C5 to fibrin-coated discs.

For each monoclonal antibody, fibrin-bearing discs prepared as described hereinafter were treated with heparinized culture supernatant (50 ul) in the absence (unfilled bar) and presence (stippled bar) of 4 mg/ml of Grade L commercial fibrinogen. Culture medium without antibodies (hatched bar) was used as negative control. Specifically bound antibody was detected with $10^5$ cpm of $^{125}$I-Goat anti-(mouse F(ab')$_2$) fragment. Each bar represents the mean of two determinations.

Figure 2:
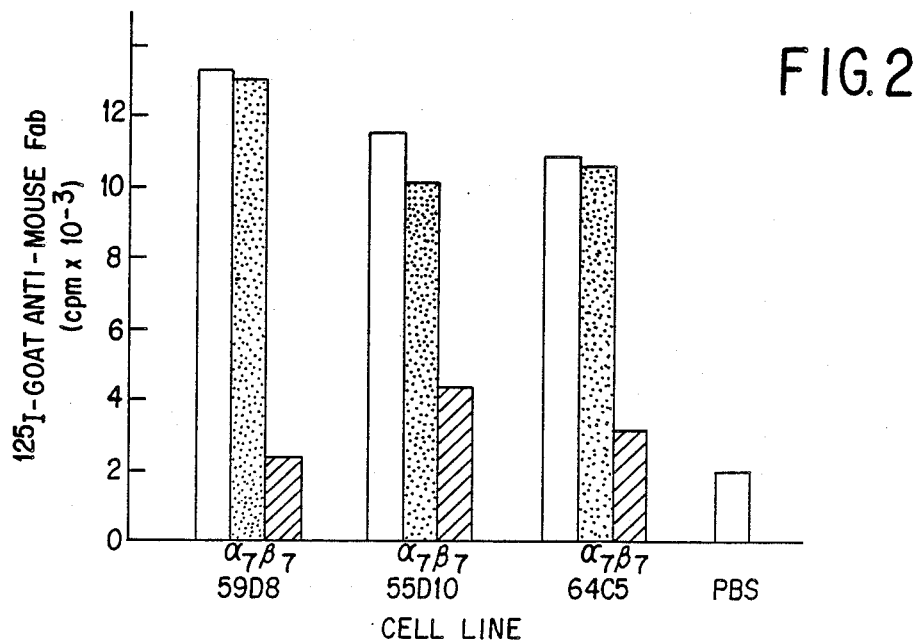

FIG. 2: Inhibition of Monoclonal Antibody Binding.

Effect of fibrin-like peptides on direct binding of monoclonal antibodies secreted by hybridoma cell lines 59D8, 55D10, and 64C5 on fibrin-coated discs.

Figure 1:
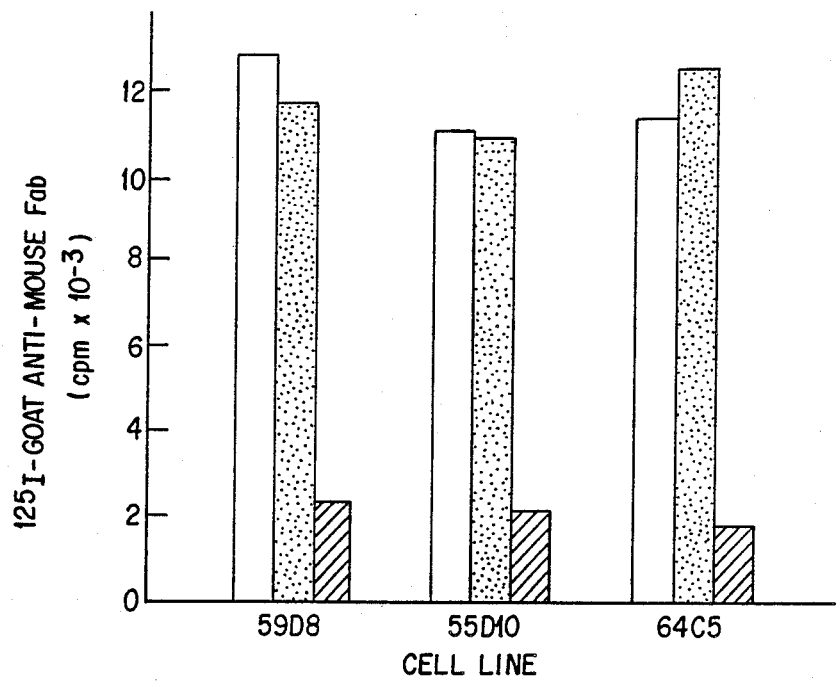
FIG. 1: Inhibition of Monoclonal Antibody Binding.

Data shown were obtained from an experiment performed as described in FIG. 1 except that the fibrin-like α-peptide, Gly-Pro-Arg-Val-Val-Glu-Arg-Cys (α$_7$, stippled bar), and β-peptide, Gly-His-Arg-Pro-Leu-Asp-Lys-Cys (α$_7$-cys, hatched bar), were used as inhibitors instead of fibrinogen (1 mg/ml in PSBA). Maximum binding (unfilled bar) was determined as a positive control in the absence of either inhibitor peptide. Each bar represents the mean of two determinations.

Figure 3:
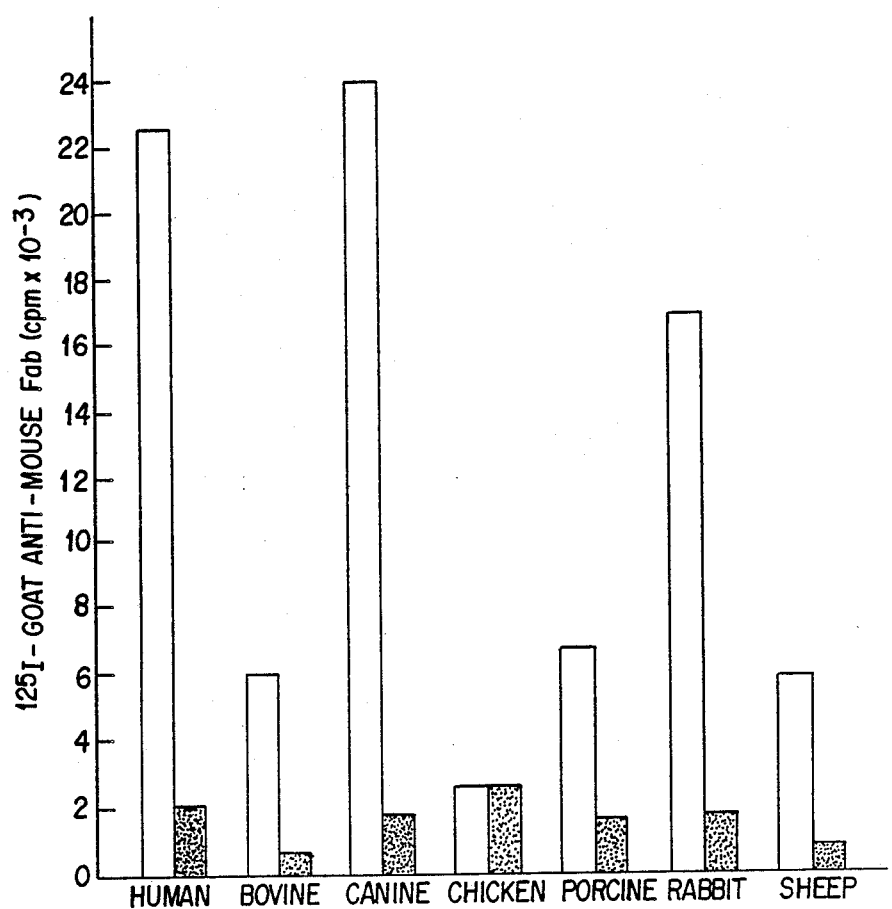

FIG. 3: Species Specificity of Monoclonal Antibody from Hybridoma 59D8.

Fibrin discs were prepared in the same manner as described for human fibrin from bovine, canine, chicken, porcine, rabbit, and sheep fibrinogens. The specifically-bound monoclonal antibody (open bars) was detected with $5 \times 10^4$ cpm of $^{125}$I-goat anti-mouse Fab fragment. Culture medium served as negative control (stippled bar). Each bar represents the mean of two determinations.

DETAILED DESCRIPTION OF THE PREFERRED EMBODIMENTS

The present invention arose from the observation that in the entire fibrin molecule there are various sequences (or epitopes), which although shared with fibrinogen, the circulating fibrin-precursor, are somewhat modified or exposed when fibrinogen is cleaved, and are thus specific to the fibrin molecule. The present inventors speculated that antibodies raised against fibrin-specific epitopes would specifically bind to fibrin, exclusive of fibrinogen. Thus, instead of using the artknown clotted fibrin as immunogen to produce the desired antibodies, synthetic peptides comprising fibrin-unique epitopic sequences are used as antigens. This immunochemical strategy emphasizes antigenic differences between fibrin and fibrinogen, and thus it substantially eliminates the antibody cross-reactivity with fibrinogen.

Peptides capable of raising fibrin-specific antibodies lacking fibrinogen cross-reactivity were synthesized, i.e., from the amino termini exposed by thrombin cleavage of the fibrinogen molecule. Some of the peptides which are capable of eliciting such antibodies are those resembling the amino-termini of human fibrin α-chain and β-chain. Some of those synthesized were the peptides containing 7 to 10 amino acids from the amino-termini.

Compounds of the presen invention comprise those having the formula:

H$_2$N-A-B-C-D-E-F-G-COR$^1$

A is gly; B is His or Pro; C is Arg; D is Pro or Val; E is Leu or Val; F is Asp or Glu; and G is Lys or Arg; (These residues can be in their protected or unprotected form, as is otherwise understood to those of skill in the art. Appropriate amino, or carboxyl protecting groups can be used (see below).)

R$^1$ is R$^2$; lys-CO-R$^2$; -lys-arg CO R$^2$; or -lys-arg-glu-CO-R$^2$;

R$^2$ is -cys-COR$^3$, OH, OM or NR$^4$R$^5$;

R$^3$ is OH, OM or NR$^4$R$^5$.

M is a pharmaceutically acceptable cation or a lower (C$_1$–C$_6$) branched or unbranched alkyl group;

R$^4$, R$^5$ are the same or different and selected from the group consisting of H or a lower alkyl group.

In other words, the compounds of the invention are peptides containing 7 to 11 amino acid residues as defined above. The preferred compounds are the peptides having 7 to 8 amino acid residues wherein R$^1$=R$^2$=OH, OM or —NR$^4$R$^5$; or R$^1$=R$^2$=cys—CO—R$^3$ where R$^3$ is OH, OM or —NR$^4$R$^5$.

When the C- terminal residue is a cysteine, the same may be substituted at the -S atom with an immunogenic protein, such as albumin, or hemocyanin. Preferred substitution is with maleimidobenzoyl or maleimidobenzoyl-keyhole limpet hemocyanin.

Useful cations M are alkaline or alkaline earth metallic cations (i.e., Na, K, Li, ½Ca, ½Ba, etc.) or amine cations (i.e., tetraalkyl ammonium, trialkylammonium, where alkyl can be C$_1$–C$_{12}$).

The variable length peptides may be in the form of the free amines (on the N-terminus), or acid-addition salts thereof. Common acid-addition salts are hydrohalic acid salts, i.e., HBr, HI, or more preferably, HCl.

The variable length peptides of this invention can be in the linear form or, in addition they may be in the form of a cyclic peptide.

Representative peptides of the present invention are:
H$_2$N-Gly-His-Arg-Pro-Leu-Asp-Lys-OH
H$_2$N-Gly-Pro-Arg-Val-Val-Glu-Arg-OH The peptides can be synthesized by the well known solid phase peptide synthesis described by Merrifield, *J. Am. Chem. Soc.* 85:2149 (1962) and Stewart and Young in *Solid Phase Peptides Synthesis* (Freeman, San Francisco, 1969) pp. 27–62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ½-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of the appropriate fractions of the column will yield the homogeneous peptide or their derivatives, which are then characterized by amino acid analysis, thin layer chromatography, high performance liquid chromatography, ultraviolet absorption spectroscopy, molar rotation, solubility, and quantitated by the solid-phase Edman degradation (Matsueda, G. R., Haber, E. and Margolies, M. N., *Biochemistry* 20: 2571 (1981)).

The technique of synthesis and isolation is fully described in the aforementioned references, as well as in U.S. Pat. No. 4,269,827, which is herein incorporated by reference. It is to be noted that during or after the synthesis, cysteines may preferably be blocked by 3,4-dimethylbenzyl (DMB), arginines and histidines by tosyl (TOS), aspartic acid and glutamic acids by benzyl (Bzl), and lysines by 2-chloro-benzyloxycarboxyl (2-CBZ).

Other protective blocking groups are well-known, and can be used in the present invention.

The techniques of sensitization and/or immunization, cell fusion, ascites production, selection of mixed hybridomas, or subcloning of monoclonal hybridomas are generally well known in the art. Attention, for example, is brought to Koprowski, et al., U.S. Pat. No. 4,172,124, Koprowski, et al., U.S. Pat. No. 4,196,265, Wands et al., U.S. Pat. No. 4,271,145, or Douillard, J. Y. and Hoffman, T., *Basic Facts about Hybridomas*, in *Compendium of Immunology*, Vol. II, L. Schwartz, ed. (1981), which are herein incorporated by reference.

In general, the purified epitopic peptides containing fibrin-specific sequences, have attached at the C-terminus a cysteine, to permit unidirectional attachment of the synthetic peptide to an immunogenic protein through a connecting bridge, e.g., maleimidobenzoylated (MB)-keyhole limpet hemocyanin (KLH). Other immunogenic conjugates can also be used, e.g., albumin, and the like. The resulting structure may have several peptide structures linked to on molecule of protein.

Lines of somatic cells immunized against the synthetic peptides can be obtained by any suitable immunization technique. The host is sensitized by administering the antigen, usually in the form of a protein conjugate, as hereinbefore indicated, by any suitable method, preferably by injection, either intraperitoneally, intravenously, subcutaneously, or by intra-foot pad. Adjuvants may be included in the immunization protocol. Virus, bacteria or other cells may also be employed.

The initial immunization with the protein bound antigen can be followed by several booster injections given periodically at intervals of several weeks. Immunized somatic cells are then obtained periodically from the host by procedures well known to those skilled in the art. The antibody contained in the plasma of each host can then be tested for its fibrin-specificity and/or lack of fibrinogen cross-reactivity. The host having the highest antifibrin response is usually most desirable as the donor of the antibody secreting somatic cells. Hyperimmunization can be effected by repeatedly injecting the additional amounts of peptide-protein conjugate by intravenous and/or intraperitoneal route.

The immunized somatic cells, preferably spleen cells, must then be fused with another cell line to produce hybridomas capable of secreting antifibrin-specific antibodies which do not cross-react with fibrinogen. Some of the factors to be considered in the selection of another cell line for fusion are rapid, uniform growth characteristics, metabolic deficiency for growth in a specified component of the growth medium, and potential for good fusion frequency. Malignant cells have been found to be particularly suitable for fusion. The species from which such cell lines are derived is also an important factor. Several cell lines including mouse, rat, hamster and human myeloma lines are available and are preferred for obtaining hybridomas. A variety of fusing agents may be employed to induce cell fusion. Polyethylene glycol and virus-induced fusions are particularly efficacious and are the preferred agents.

Preferred conditions for the somatic cell fusion and establishment of the hybridoma cell lines are those reported by Kohler and Milstein, *Nature* (London) 256:496 (1975), which is herein incorporated by reference.

Preferred hosts for the production of somatic cells are mouse, in particular BALB/c, or AJ. Particularly suited malignant cells for the purpose of establishing hybridoma cell lines by somatic cell fusion are myeloma cell lines, in particular the Sp2/0 and NS-1 lines.

Rapid identification of suitable hybrids is a key procedure in all hybridoma work. Early detection of hybridoma antibodies may be performed by any suitable assay; particularly preferred are radioimmunoassays, enzyme-immunoassays, and the like. Preferred is a radioimmunoassay utilizing fibrin-coated microtiter wells exposed to the antibody containing sample premixed with human fibrinogen, and then exposing the antigen antibody complex to radiolabelled anti-Fab fragment antibody (See, Klinman et al., *Ann. Immunol.* (Paris) 127C: 489 (1976), which is herein incorporated by reference).

The binding of antibodies to cross-linked human fibrin, i.e., aggregated fibrin monomers, can also be tested. Because clotted fibrin is mechanically difficult to manipulate in a quantitative manner, human fibrinogen can be clotted on filter paper discs by adding human thrombin. The fibrin-coated discs can then be treated in the same manner as the fibrin-coated microtiter wells, hereinbefore described.

Maintenance of the hybridomas is accomplished by the use of appropriate selection growth medium. Standard tissue culture medium together with feeder cells are usually preferred. Hybrids may also be grown in horse or calf serum or in serum-free media, and the like.

Hybrids obtained by fusion are heterogenous colonies. In order to get a homogeneous line expressing a given function, these colonies are preferably cloned. By cloning is meant the process of achieving growth of a cell line from a single parental cell, viz., a monoclonal expansion. Such cloning may be achieved by any suitable technique, such as by agarose technique and the like.

Antibody secreting hybrids grown in tissue culture flasks yield supernatants with variable concentrations of antibody, usually in the range of about 1-30 ug/ml. Higher yields are, therefore, obtained preferably by transferring hybrids into animals with inflammatory ascites. Ascites are preferably induced by intraperitoneal injection of the hybridoma or by other suitable methods.

Preservation of the hybridoma is important and may be accomplished by any suitable technique. A preferred method is by subcloning or by freezing adequate amounts of the hybridoma early after fusion, and to reclone the cell population, as needed.

The term "hybridoma," as used herein, refers to hybrid cells obtained by the technique of somatic cell fusion, as described in the specification, the hybrid so obtained having the capability of producing antifibrin-specific antibodies lacking fibrinogen cross-reactivity.

The term "monoclonal antibodies," as used herein, refers to antibodies produced by a homogenous line of a cloned colony of cells, derived from a single parental hybridoma.

Once the monoclonal hybridoma has been prepared, it is a matter of routine in the art to isolate the desired antibodies from the supernatant. Well known techniques, such as salt precipitation, gel chromatography, ion exchange chromatography, affinity chromatography, and the like, can be used to obtain the antibodies in substantially pure form. By "substantially pure form," it is meant that the antibodies are essentially free from non-monoclonal antibody impurities, such as other proteins, other antibodies having different specificities, nucleic acids, polysaccharides, cell fragments, and the like. The antibodies can be used in soluble form or can be immobilized on an aqueous and soluble solid-phase, to obtain insolubilized antibodies.

The term "epitope," as used herein, refers to specific amino acid sequences characteristic of a protein, in which sequences arranged in a characteristic configuration can elicit antibodies which bind specifically to said sequences, in the configuration in which they appear (e.g., fibrin molecule), said antibodies not being capable of binding to the same amino acid sequence when it appears in a different configuration (e.g., fibrinogen molecule).

The antibodies produced by the method of the present invention can be utilized in any of a myriad of applications normally described for such antibodies. For example, these antibodies can be used in the development of a radioimmunoassay or enzyme-linked immunoassay for fibrin in the presence of fibrinogen or other proteins. They can most preferably be used as immunoaffinity ligands for the purification of fibrin. They can also be used for the in vitro detection of fibrin in clinical samples, for the in vivo localization of vascular thrombi or fibrin deposits, in linkage to drugs, and the like.

One or more of the monoclonal antibodies of the invention are particularly suited for use in in vitro and in vivo immunodiagnosis. For in vitro diagnosis the antibodies can be utilized in liquid phase or bound to a solid phase carrier. In addition, the monoclonal antibodies in these immunoassays can be detectably labeled in various ways.

There are many carriers to which the monoclonal antibodies of the invention can be bound and which can be used in detecting the presence of the fibrin. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding monoclonal antibodies or will be able to ascertain such, using routine experimentation.

The term "antibodies" as used in this invention is meant to include intact molecules as well as fragments thereof, such as for example, Fab and F(ab')$_2$, which are capable of binding antigen.

There are many different labels and methods of labeling known to those of ordinary skill in the art. Examples of the types of labels which can be used in the present invention include enzymes, radioistopes, fluorescent compounds, chemiluminescent compounds, bioluminescent compounds, and metal chelates. Those of ordinary skill in the art will know of other suitable labels for binding to the monoclonal antibodies, or will be able to ascertain such, using routine experimentation. Furthermore, the binding of these labels to the monoclonal antibodies can be done using the standard techniques common to those of ordinary skill in the art.

One of the ways in which a monoclonal antibody of the invention can be detectably labeled is by linking the monoclonal antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label are malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of the detectably labeled monoclonal antibody can also be detected by labeling the monoclonal antibody with a radioactive isotope. The presence of the radioactive isotope can then be determined by such means as the use of a gamma counter or a scintillation counter. Isotopes which are particularly useful are $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe, and $^{75}$Se.

It is also possible to detect the binding of detectably labeled monoclonal antibodies by labeling the monoclonal antibody with a fluorescent compound. When the fluorescently labeled monoclonal antibody is exposed to light of the proper wavelength, its presence can then be detected due to the fluorescence of the dye. Among the most commonly used fluorescent labeled compounds are fluorescein isothiocyanate, rhodamine, phycoerythrin, phycocyanin, allophycocyanin, o-phthalaldehyde, and fluorescamine.

The monoclonal antibodies of the invention can also be detectably labeled using fluorescence emitting metals such as, $^{152}$Eu, or others of the lanthanide series. These metals can be attached to the antibody molecule using such metal chelating groups as diethylenetriaminepentaacetic acid (DTPA) or ethylene diaminetetraacetic acid (EDTA).

Another way in which the monoclonal antibody can be detectably labeled is by coupling it to a chemiluminescent compound. The presence of the chemiluminescent-tagged monoclonal antibody is then determined by detecting the presence of luminescence that arises during the course of the chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used to label the monoclonal antibody. Bioluminescence is a special type of chemiluminescence which is found in biological systems and in which a catalytic protein increases the efficiency of the chemiluminescent reaction. The presence of the bioluminescently labeled monoclonal antibody would be determined by detecting the presence of luminescence. Important bioluminescent compounds for purposes of labeling are luciferin, luciferase, and aequorin.

For purposes of the invention, the fibrin which is detected by antibody of the invention may be present in biological fluids and tissues. Any sample containing a detectable yet unknown amount of fibrin can be used. Normally, a sample is a liquid such as, for example, urine, saliva, cerebrospinal fluid, blood, serum and the like, or a solid or semi-solid such as for example, tissues, feces, and the like.

Another technique which may also result in greater sensitivity consists of coupling the antibodies to low molecular weight haptens. These haptens can then be specifically detected by means of a second reaction. It is common, for example, to use such haptens, as biotin (reacting with avidin) or dinitrophenyl, pyridoxal, and fluorescamine (reacting with specific anti-hapten antibodies) in this manner.

For diagnostic in vivo imaging, the type of detection instrument available is a major factor in selecting a given radionuclide. The radionuclide chosen must have a type of decay which is detectable for a given type of instrument.

Another important factor in selecting a radionuclide for in vivo diagnosis is that the half-life of the radionuclide be long enough so that it is still detectable at the time of maximum uptake by the target, but short enough so that after diagnosis unwanted radiation does not remain in the host. Ideally, a radionuclide used for in vivo imaging will lack a particulate emission, but produce a large number of photons in the 140–200 keV range.

For in vivo diagnosis and/or imaging radionuclides may be bound either directly or indirectly by using an intermediary functional group. An intermediary group which is often used to bind radioisotopes which exist as metallic cations to antibodies is DTPA. Typical examples of metallic ions which can be bound to antibody molecules and used for in vivo diagnosis are $^{99m}Tc$, $^{123}I$, $^{131}I$, $^{111}In$, $^{97}Ru$, $^{67}Cu$, $^{67}Ga$, $^{68}Ga$, $^{72}As$, $^{89}Zr$, and $^{201}Tl$.

The monoclonal antibodies of the invention can also be labeled with paramagnetic isotopes for purposes of in vivo diagnosis. Examples of elements which are particularly useful (as in Magnetic Resonance Imaging (MRI) techniques) in this manner are $^{157}Gd$, $^{55}Mn$, $^{162}Dy$, $^{52}Cr$, and $^{56}Fe$.

The dose ranges for the administration of the antibody are those large enough to detect the presence of thrombi. The dosage should not be so large as to cause adverse side effects, such as unwanted cross reactions, and anaphylactic reactions and the like. Generally, the dosage will vary with the age, condition, sex, and extent of disease in the patient, counter indications, if any, immune tolerance and other such variables, to be adjusted by the individual physician. Dosage can vary from 0.01 mg/kg to 500 mg/kg, preferably 0.01 mg/kg to 200 mg/kg. The antibody(ies) can be administered parenterally by injection or by gradual perfusion over time. It can be administered intravenously, intraperitoneally, intramuscularly, or subcutaneously.

Preparations for parenteral administration include sterile aqueous or non-aqueous solutions, suspensions, and emulsions. Examples of non-aqueous solvents are propylene glycol, polyethylene glycol, vegetable oil such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intraveneous vehicles include fluid and nutrient replenishers, electrolyte replenishers, such as those based on Ringer's dextrose, and the like. Preservatives and other additives may also be present, such as for example, antimicrobials, anti-oxidants, chelating agents, and inert gases and the like. See, generally, *Remington's Pharmaceutical Science*, 16th ed., Mac Eds., 1980.

The monoclonal antibodies of the invention are ideally suited for the preparation of a kit. Such a kit may comprise a carrier means being compartmentalized to receive in close confinement one or more container means such as vials, tubes, and the like, each of said container means comprising the separate elements of the immunoassay or imaging method to be used. The types of immunoassays which can be incorporated in kit form are many. Typical examples of some of the immunoassays which can utilize the antibodies of the invention are competitive immunoassays and immunometric, or sandwich immunoassays.

Monoclonal antibodies of the invention for in vivo purposes may be present in a kit in detectably labeled form or may be detectably labeled at some later time. For example, such a kit can contain the monoclonal antibodies of the invention coupled to a chelating group such as DTPA, and at time of use these antibodies are mixed with a metallic ion, such as $^{99m}Tc$ to detectably label the monoclonal antibodies. In this way, a radioisotope with short half-life can be more effectively and economically utilized.

Having now generally described this invention, the same will become more readily understood by reference to specific examples included herein for purposes of illustration only, and is not intended to be limiting unless otherwise specified.

EXAMPLES

EXAMPLE 1

Synthesis of the NH$_2$-terminus Peptide of Fibrin $\beta$-Chain ($\beta_7$-peptide).

Synthesis was started with the esterification of Boc-Cys(Dmb) (5 mmol; 1.695 g) to 5 g hydroxymethyl resin using dicyclohexylcarbodiimide (DCC) (5 mmol; 1.031 g) as the coupling reagent and dimethylaminopyridine (DMAP) (5 mmol; 0.61 g) as the catalyst, in 12 ml dimethylformamide (DMF) as a solvent. The remaining hydroxyl groups were benzoylated using benzylchloride (0.3M) and pyridine (0.4M) in 84 ml dichloromethane (DCM). The resulting resin contained 0.30 mmol of cysteine per g.

Using the Merrifield solid-phase method supra, the first seven amino acid residue of the fibrin $\beta$-chain were assembled on the Cys(Dmb)-OCH$_2$-resin in a stepwise fashion. The completeness of coupling and Boc-removal reactions were monitored by the ninhydrin test on a peptide-resin sample removed from the reaction mixture. No recoupling was necessary in any of the coupling cycles.

A general synthetic protocol for each coupling cycle is shown below:
1. Incorporation of Boc-amino acid
   (a) Wash resin 3x with 25 ml DCM.
   (b) Dissolve 5.0 equivalents Boc-amino acid in 10 ml DCM and add the resulting solution to the neutralized resin, then add 5.0 equivalents DCC (1.0M in DCM) and stir for 2 hrs at room temperature. Before Lys(2-ClZ).TBA and Boc-His(Tos).DCHA are used in coupling, they are quantitatively converted to the free acids by shaking a solution in DCM with 1N H$_2$SO$_4$.
   (c) Ninhydrin test on resin sample.
2. Removal of Boc group
   (a) Wash resin 3x with DCM.
   (b) Add 25 ml TFA (25% trifluoroacetic acid in DCM), stir for 1 min.
   (c) Repeat TFA treatment for 30 min.
   (d) Wash resin 3x with DCM.
   (e) Ninhydrin test.
3. Neutralization
   (a) Add 25 ml TEA (10% triethylamine in DCM), stir 1 min.
   (b) Repeat TEA treatment for 5 min.

A sample of the completed peptidyl-resin, having the sequence Gly-His(Tos)-Arg-(Tos)-Pro-Leu-Asp(Bzl)-Lys(2-ClZ)-Cys(3,4-Dmb)-OCH$_2$-resin, was subjected to solid-phase Edman degradation to confirm the amino acid sequenc and quantitate the components (Edman, supra). The average level of amino acid deletions, expressed as % preview per cycle, was less than 1% (Niall, H. D., et al., in *Chemistry and Biology of Peptides* (Ann Arbor Sciences, Ann Arbor, 1972, p. 695), and Matsueda, G., et al., *Biochemistry* 20: 2571 (1981), incorporated herein by reference). The peptide Gly-His-Arg-Pro-Leu-Asp-Lys-Cys ($\beta_7$-cys) was released from the resin upon HF cleavage at 0° C. for 30 min. in the presence of 10% anisole. The HF product mixture was washed with anhydrous ether. The free peptide was extracted with 1M acetic acid and lyophilized.

The fully deprotected peptide gave the following amino acid composition upon acid hydrolysis: Asp, 1.05[1]; Pro, 1.01[1]; Gly, 0.98[1]; Leu, 1.01[1]; His, 0.90[1]; Lys, 1.03[1]; and Arg, 1.02[1]. Values were not obtained for Cys because of its lability to acid hydrolysis.

EXAMPLE 2

Preparation of $\beta_7$-Peptide-Protein Conjugate

The $\beta_7$-peptide synthesized in Example 1 was then covalently coupled to maleimidobenzoylated keyhole limpet hemocyanin (MB-KLH) as described by Kitagawa, T. and Aikawa, T. (*J. Biochem.* (Japan) 79: 233 (1976), and Lerner, R. A., et al., *Proc. Natl. Acad. Sci., USA*, 78: 3404 (1981), and incorporated herein by reference). The coupling reaction was monitored by titrating the remaining sulhydryl groups by the method described by Ellman, G. L. (*Arch. Biochem. Biophys.*, 82: 70 (1959), and incorporated herein by reference).

Briefly, 40 mg keyhole limpet hemocyanin (KLH) (Schwarz/Mann) was dissolved in 2 ml phosphate buffer, pH 6. Then 40 mg m-maleimidobenzoyl-succinimide ester (MBS) (Pierce Chemical Co.) was added. The mixture was stirred for 7 hr at room temperature. The reaction mixture was filtered through filter paper. The filtrate was dialysed against 4 liters phosphate buffer, pH 6, overnight at 4° C. The dialysate (3.4 ml) which contained 36.3 mg MB-KLH was used to couple to the $\beta_7$-peptide.

$\beta_7$-peptide (20 mg) in 1 ml isotonic saline was added to 3.4 ml of the MB-KLH solution. Tris base buffer (1M) was added until the mixture reached pH 8, and was stirred at room temperature for 4 hr. The reaction was monitored by titrating the remaining sulfhydryl group. The unreacted peptide was removed by dialysis and the conjugate was further purified by gel filtration on a Sephadex G-25 column.

EXAMPLE 3

Immunization of BALB/c Mice.

For the purpose of fusion, three female BALB/c mice were immunized ten weeks prior to fusion with 30 ug of $\beta_7$-peptide-MB-KLH conjugate. A single booster injection was given intraperitoneally four weeks later. The plasma of each mouse obtained from tail bleeding contained antibodies which reacted with human fibrin monomer, even when fibrinogen was present at a concentration of 4 mg/ml, as determined by the radioimmunoassay (RIA) described in Example 5. The mouse with the highest antifibrin response was chosen as the donor mouse in a somatic cell fusion experiment. For three consecutive days prior to the somatic cell fusion experiment, that mouse was hyperimmunized with 50 ug conjugate which was divided between intravenous and intraperitoneal administrations.

EXAMPLE 4

Somatic Cell Fusion.

Hybridoma cell lines were established from a somatic cell fusion experiment as described by Kohler, G., and Milstein, C. (*Nature* (London) 256: 496 (1975), which is herein incorporated by reference), using the Sp2/0 myeloma cell line and immune spleen cells from a female BALB/c mouse immunized as described in Example 3.

Briefly, the immune spleen was harvested from the donor mouse. The lymphocytes were teased from the capsule and dispersed into a suspension in 10 ml low glucose Dulbecco's Modified Eagles Medium (DMEM), centrifuged at 1200 rpm for 7 min. and resuspended in DMEM containing 4.5 gm glucose, 0.6 gm L-glutamine, 50 mg Gentamicin and 167 ml fetal calf serum per liter (20% FCS). The lymphocyte suspension was mixed with an equal volume of lipopolysaccharide (LPS) solution (40 ug LPS/ml, 20% FCS) and cultured for 6 hr in a humidified incubator at 37° C. in an atmosphere of 7% $CO_2$. The LPS stimulated spleen cell preparation was mixed with approximately $5 \times 10^7$ mouse myeloma cells (Sp2/0) at a ratio 2:1, centrifuged to remove supernatant, resuspended in DMEM and centrifuged again to remove supernatant. The tube was tapped to disperse the cell pellet. These cells were treated with 1 ml of polyethylene glycol (Sigma; MW=1000; 30% in DMEM, v/v, neutral pH) for 7 min. During the 7 min period, the cell mixture was centrifuged at 1200 rpm for 4 min. Thereafter, 80 ml HAT media (0.32 mg thymidine, 1.13 mg hypoxanthine and 0.015 mg aminopterin per 100 ml, 20% FCS) was added to eight 96-well tissue culture plates containing macrophage feeder layer (4000 macrophages in 0.1 ml HAT per well). Starting from the second week after the fusion experiment, the wells were fed routinely with HT media (0.32 mg thymidine and 1.13 mg hypoxanthine per 100 ml, 20% FCS).

The wells were screened visually for cell growth, and the culture media screened for antifibrin antibody in the presence of fibrinogen by the radioimmunoassay, infra.

EXAMPLE 5

Solid-Phase Radioimmunoassay for Antifibrin Antibody

The radioimmunoassay used for screening culture media from fusion wells for antifibrin antibody in the presence of fibrinogen is based on that reported by Klinman, N. R., et al., *Ann. Immunol.*, supra. Briefly, wells of polyvinyl chloride (PVC) microtiter plates (Cooke Industries) were coated with 25 ul of a solution of human fibrin monomer (1 mg/ml, in 3.3M urea) for 14 hr. (The human fibrin monomer was prepared by clotting 49 mg fibrinogen (grade L, Kabi, Stockholm, Sweden) in 20 ml phosphate buffer with 10 NIH units of thrombin. The clot collected was dissolved in 3.3M urea). After 14 hours at 4° C., unabsorbed human fibrin monomer solution was removed from the wells and the plates were extensively washed with water. To minimize nonspecific binding, the antigen coated wells were filled with 25%-globulin-free horse serum in phosphate buffer for 1 hr. at room temperature. The buffer, pH 7.4, contained 100 U heparin, 400 KIU Trasylol per ml neat horse serum and a final concentration of 3 mM freshly dissolved phenylmethylsulfonyl fluoride (PMSF). The plates were again extensively washed with water. Then aliquots of culture medium, serum or plasma were premixed with an equal volume of Grade L human fibrinogen (Kabi, Stockholm) at a concentration of 8 mg/ml in phosphate buffer saline with azide (PBSA), pH 7.4, for 30 minutes. Twenty-five ul of samples thus prepared were then placed in the antigen coated wells and incubated for two hr. at room temperature. After washing, the plates were incubated for one hr. with 50 ul of $^{125}$I-Goat anti-mouse Fab fragment (100 kcpm/50 ul). After rinsing, wells were dried and the radioactivity determined in a gamma counter.

Radioiodination was carried out by the chloramine-T method (Greenwood, F. C., Hunter, W. M. and Glover, J. S., *Biochem. J.* 89: 114 (1963)), at a ratio of 1.0 mCi of $^{125}$I to 50 ug of purified antibody.

EXAMPLE 6

Determination of Immunoglobulin Isotype.

Immunoglobulin isotype was determined by enzyme-linked immunoabsorbent assay (ELISA) employing the Mouse Immunoglobulin Subtype Identification Kit (Boehringer Mannheim Biochemicals, Indianapolis, Ind.).

EXAMPLE 7

Selection of the Clones.

After 11 days in primary culture, 13 microtiter wells contained cells which multiplied to become confluent. Aliquots of culture medium from those wells were withdrawn, mixed with heparin and PMSF. Thirty min. after mixing an equal volume of human fibrinogen (8 mg/ml in PBSA) with the heparinized aliquot, the mixture was tested on fibrin monomer-coated microtiter wells, as described above. Antifibrin activity was detected in 3 of 13 of the samples. Seven of the remaining samples contained anti-KLH activity, and none of the samples contained both activities. After 20 days in primary culture, 12 of 72 confluent wells containing hybridoma cell lines had antifibrin immunoreactivity that was not inhibited by fibrinogen when tested by the RIA method described above. Seven cell lines were arbitrarily selected for cloning by a limiting dilution method, but only three continued to yield antifibrin-producing hybridomas. The stability and monoclonality of these three cell lines were demonstrated by recloning each cell line at limiting dilution. Ninety percent of the recloned cell lines continued to yield fibrin-specific antibodies when tested by the RIA of Example 5. The isoelectric points of three monoclonal antibodies, hybridomas 55D10, 59D8 and 64C5, were 6.50, 6.40 and 7.60 respectively. The isotype of all three monoclonal antibodies was gamma-1(heavy chain) and kappa (light chain).

EXAMPLE 8

Binding of Anti-Fibrin Antibodies to Cross-Linked Human Fibrin

After the binding of anti-fibrin antibodies to human fibrin monomer in the presence of fibrinogen was established, the binding to cross-linked human fibrin was tested.

Briefly, 9.5 mm discs of filter paper (Bunn Coffee Filter, 365 C St., Boston, Mass.) were used as solid support. On each paper disc, 20 ul of human fibrinogen (40 ul in 20 ul; Kabi grade L, Stockholm, Sweden) was clotted by adding 25 ul of human thrombin (1.25 U, Sigma, St. Louis, Mo.) in the presence of 20 mM CaCl$_2$ and Trasylol (0.05 KIU/ 1, Mobay) at room temperature for 2 hr. Thereafter, the fibrin-discs were washed exhaustively with PBSA, and stored at 4° C. in a solution containing 10 mM KH$_2$PO$_4$, 0.15M NaCl, 0.02% NaN$_3$ (PBSA) and 50 KIU/ml Trasylol. The absorbance of the solutions before and after clotting was measured at 280 nm and the clotting efficiency was calculated to be 80%.

When the fibrin discs were stained with Coomassie Brilliant Blue dye solution, only those filters in which thrombin had been used in the clotting mixture were strongly stained, indicating the presence of aggregated fibrin monomers. The results of these studies, shown in FIG. 1, indicate that the monoclonal antibodies from the 3 hydridoma cell lines 59D8, 55D10 and 64C5 bound to the fibrin-coated discs, confirming antibody recognition of aggregated fibrin monomers. When human fibrinogen (4 mg/ml) was tested as inhibitor, the binding of all three monoclonal antibodies was substantially unaffected (stippled bar). Controls lacking antibodies show a minimal amount of binding (hatched bar). In contrast, a control Dig-26-10 anti-digoxin (Hunter, M. M., et al., *J. Immunol.* 129: 1165 (1982)), when substituted in place of the anti-$\beta_7$-peptide monoclonal antibodies, did not bind to fibrin discs (2390±20 cpm, data not shown).

Specifically bound antibody was detected by adding 10$^5$ cpm (25 ul) of $^{125}$I-Goat anti-mouse Fab fragment.

EXAMPLE 9

Specificity Determination

Since the hybridomas were selected on the basis of fibrin monomer specificity, peptide inhibition of binding by the monoclonal antibodies was of interest. Thus, the effect of fibrinlike peptides on the direct binding of monoclonal antibodies, 59D8, 55D10 and 64C5, on fibrin-coated discs was tested in an assay similar to the one described before. In this experiment, as shown in FIG. 2, another fibrin-like peptide, Gly-Pro-Arg-Val-Val-Glu-Arg-Cys ($\alpha_7$) (stippled bar), and the $\beta_7$-peptide, Gly-His-Arg-Pro-Leu-Asp-Lys-Cys (hatched bar), each in 1 mg/ml PBSA, were used as inhibitors instead of fibrinogen. Maximum binding (unfilled bar) was determined in the absence of either inhibitor peptide as a positive control. The results indicate that the synthetic $\beta$-fibrin peptide inhibited binding of the three monoclonal antibodies, whereas the $\alpha_7$ peptide did not. These results confirm that the fibrin-specific monoclonal antibodies were elicited against the synthetic $\beta_7$-peptide fibrin-like antigen and were not fortuitously selected by the radioimmunoassay screening procedure described in Example 5.

EXAMPLE 10

Species Specificity of Antibodies Secreted by Cell Line 59D8

The species specificity of antifibrin monoclonal antibody 59D8 was examined using the fibrin-disc assay. Fibrin discs were prepared in the same manner as described for human fibrinogen from bovine, canine, chicken, porcine, rabbit and sheep fibrinogens. On separate discs the fibrinogens of the different species clotted as described above. Each fibrin-bearing disc was treated with 50 ul of heparinized culture supernatant. The specifically-bound monoclonal antibody (open bars) was detected with 5×10$^4$ cpm (25 ul) $^{125}$I-Goat anti-mouse Fab fragment. This monoclonal antibody cross-reacted strongly with canine and rabbit clotted fibrin, partially with bovine, porcine, and ovine fibrin, while showing virtually no binding to chicken fibrin. Negative controls (stippled bar) were prepared in each case by substituting blank culture medium in place of the antibodies prior to the addition of the $^{125}$I-Goat anti-mouse Fab fragment. The results of this test are shown in FIG. 2.

EXAMPLE 11

Ex vivo Circulatory Model for Human Fibrin Detection

An ex vivo circulatory model was devised in order to avoid cross-reactivity with spontaneously formed thrombi in the experimental animal. An extracorporeal chamber was attached via cannulae to the carotid artery of a chicken on one end and the contralateral jugular vein at the other end, and maintained at 37° C. in a water bath. At the start of the experiment, 50 ug of monoclonal antibody was injected into the jugular vein via the efferent cannula. Blood was then permitted to circulate through the chamber for 15 minutes. The ex vivo circulation was temporarily interrupted to permit the insertion into the extracorporeal chamber of two fibrin-clotted discs, each rolled into an S-shaped configuration. The circulation was again interrupted to remove the fibrin-clotted discs, at different times (10, 30 and 60 min). The discs were immediately washed with an excess of PBSA containing 5 KIU/ml of Trasylol. The bound monoclonal antibody was measured by in vitro incubation of the fibrin discs for one hour with $^{125}$I-Goat anti-mouse Fab antibody.

Table I presents data obtained for the monoclonal antibody from hybridoma 64C5. However, similar results were obtained using antibody from hybridoma cell line 59D8. In Experiment I, discs containing 30–35 ug human fibrin were placed in the chamber and exposed to intravenously administered 64C5 antibodies (50 ug) prior to in vitro treatment with a radioiodinated second antibody. In Experiment II, the human fibrin-coated discs were subjected to plasminolysis in the ex vivo chamber. The discs were then removed from the chamber, assayed for residual fibrin using monoclonal antibody from the hybridoma cell line 64C5, and then qualified with the radioiodinated second antibody, as described before. Data listed are the mean of two separate determinations, deviation from mean.

TABLE I

Detection of Human Fibrin, Chicken ex vivo Circulatory Model

| Experiment | Paper Disc | Circulation ex vivo (min) | Counts/min |
| --- | --- | --- | --- |
| I. Ex vivo detection of fibrin discs by I.V.-administered antibody 64C5 | Fibrin-coated | 0 | 1935 250 |
| | Fibrin-coated | 10 | 13116 450 |
| | Fibrin-coated | 30 | 15395 600 |
| | Uncoated | 60 | 442 60 |
| II. Stability of fibrin toward ex vivo circulation: in vitro assessment with antibody 64C5 | Fibrin-coated | 0 | 19138 570 |
| | Fibrin-coated | 10 | 18697 600 |
| | Fibrin-coated | 30 | 19512 500 |
| | Fibrin-coated | 60 | 18732 500 |

The results of these experiments show that:

(i) the binding of intravenously injected 64C5 or 59D8 monoclonal antibody to fibrin discs rapidly exceeds 50% within 10 minutes, as compared to the maximum value for control fibrin discs which were immersed in the solution of the same antibody titer in vitro, and (ii) fibrin discs exposed to circulating chicken blood for one hour did not differ from unexposed fibrin discs in their binding of 64C5 or 59D8 antibody (results not shown).

In control ex vivo experiments, it was demonstrated that:

(iii) filter paper discs which did not contain human fibrin failed to bind antibody when placed in the ex vivo chamber, (iv) under the same circumstances, fibrin discs did not bind $^{125}$I-goat anti-mouse Fab IgG when the monoclonal antibody was not injected; and (v) human fibrin discs could be exposed to circulating blood of anesthetized chickens for two hours without loss of antibody recognition.

Thus, monoclonal antibodies elicited by a synthetic peptide of the type disclosed here, based on the human fibrin sequence, are capable of binding to human fibrin monomer, as well as to fibrin polymer, in the presence of fibrinogen. These experiments have shown, both in in vitro and ex vivo experimental models, the specificity of the antibody raised against these peptides and its lack of cross-reactivity with fibrinogen.

EXAMPLE 12

Detection of Pulmonary Emboli

Experimental thrombi were formed in an isolated segment of the jugular vein of dogs by mixing thrombin, canine blood, and $^{125}$I-fibrinogen. After one hour, the restraining ligatures were removed to release the $^{125}$I-thrombi which could be found in the lungs by imaging for $^{125}$I activity using a gamma-radiation camera. After one hour, monoclonal antibody 64C5, radiolabeled with $^{111}$In via DTPA residues (1.5–2 mCi/4–10 mg antibody protein) was injected intravenously and the lungs imaged for the next 24 hours. After 24 hours, the animals were sacrificed and the lungs imaged ex vivo for $^{125}$I and $^{111}$In activities. The excised lungs were examined by gross inspection, then sliced to ascertain the location of the emboli in the lungs. In addition, tissues samples were obtained for scintillation counting. Control animals (n=3) were treated identically except that they were injected with 4mg $^{111}$In-labeled non-fribrin specific IgG$_1$ monoclonal antibody. Discrete in vivo localization was found in four of six experimental animals injected with $^{111}$In-64C5 in areas were the emboli were located. This was confirmed by gross visual inspection of the excised lungs. Control animals did not show localization in the areas of pulmonary emboli, even in the images of the excised lungs. Thus, this study demonstrates the potential of fibrin-specific monoclonal antibody for the non-invasive localization and visualization of in vivo emboli.

EXAMPLE 13

Gel Electrophophoresis of Anti-peptide Monoclonal Antibodies

The isolectric points of the monoclonal antibodies listed above were determined on LKB Ampholine PAG plates (LKB-Produkter AB, Box 305, S-161 26 Bromma, Sweden) following the procedure described in the package insert.

Hybridomas 59 D8, 64C5 and 55D10 were deposited for 30 years at the American Type Culture Collection (ATCC), 12301 Parklawn Drive, Rockville, Md. USA 20852, on Apr. 20, 1984, and assigned the following accession numbers:

59D8: ATCC No. HB 8546;
64C5: ATCC No. HB 8545; and
55D10: ATTC No. HB 8547.

It is understood that these descriptions, examples and embodiments are for illustrative purposes only and that various modifications will be suggested within the spirit and perview of this application and the scope of the appended claims.

What is claimed is:

1. A process for producing monoclonal anti-fibrin specific antibodies, devoid of cross reactivity with fibrinogen comprising:
    a. obtaining lymphocytes from a animal immunized against the peptide fragment comprising

A-B-C-D-E-F-G attached to a suitable immunogenic carrier, wherein

A is glycine;
    B is histidine or proline;
    C is arginine;
    D is proline or valine;
    E is aspartic acid or glutamic acid;
    G is lysine or arginine;
    b. fusing said lymphocytes with a meyloma cell line to produce hydridomas which secrete anti-fibrin specific antibodies substantially devoid of fibrinogen cross-reactivity;
    c. cultivating said hybridomas; and
    d. isolating said secreted antibodies.

2. The process of claim 1, wherein said lymphocytes are comprised of spleen cells.

3. The process of claim 2, wherein said spleen cells are mice spleen cells.

* * * * *